US008476433B2

(12) United States Patent
Granik et al.

(10) Patent No.: US 8,476,433 B2
(45) Date of Patent: Jul. 2, 2013

(54) AGENT EXHIBITING THE PROPERTIES OF A COGNITIVE FUNCTION PROMOTER (EMBODIMENTS)

(75) Inventors: Vladimir Grigorevich Granik, Moscow (RU); Vladimir Vladimirovich Granik, legal representative, Moscow (RU); Valery Aleksandrovich Parshin, Moscow (RU); Tatyana Vasilyevna Golovko, Odintsovo (RU); Nelya Zarifovna Tugusheva, Moscow (RU); Marina Igorevna Medvedeva, Moscow (RU)

(73) Assignee: Unikorm, Tomskaya OBL. (RU)

( * ) Notice: Subject to any disclaimer, the term of this patent is extended or adjusted under 35 U.S.C. 154(b) by 0 days.

(21) Appl. No.: 13/695,257

(22) PCT Filed: Apr. 28, 2011

(86) PCT No.: PCT/RU2011/000276
§ 371 (c)(1),
(2), (4) Date: Dec. 27, 2012

(87) PCT Pub. No.: WO2011/136700
PCT Pub. Date: Nov. 3, 2011

(65) Prior Publication Data
US 2013/0131342 A1   May 23, 2013

(30) Foreign Application Priority Data

Apr. 30, 2010 (RU) ................................ 2010117541

(51) Int. Cl.
*C07D 401/12* (2006.01)
*C07D 471/04* (2006.01)
(52) U.S. Cl.
USPC .......................................... 544/300; 546/122
(58) Field of Classification Search
USPC .......................................... 544/300; 546/122
See application file for complete search history.

(56) References Cited

U.S. PATENT DOCUMENTS 6,831,087 B2   12/2004  Alanine et al.
2006/0211731 A1*   9/2006  Meth-Cohn et al. .......... 514/314

FOREIGN PATENT DOCUMENTS

EA     20080001639    8/2009
EP         1736155   12/2006
WO         9118607   12/1991
WO       2006032470    3/2006

OTHER PUBLICATIONS

N.I. Andreeva at al., "New Data on the Psychopharmacological Properties of the Antidepressant Azaphen", © 1997 Plenum Publishing Corporation, Mar. 1997, vol. 31, No. 3, pp. 116-119.

Bachurin S.O., "Issues of Medical Chemistry", 2001, No. 2, pp. 1-41.
P. Camps at al., "Cholinergic Drugs in Pharmacotherapy of Alzheimer's Disease", © 2002 Bentham Science Publishers, Ltd., Mini Reviews in Medicinal Chemistry, 2002, vol. 2, No. 1, pp. 11-25.
R. Cumin at al., "Effects of the Novel Compound Aniracetam (Ro 13-5057) Upon Impaired Learning and Memory in Rodents", Psychopharmacology © Springer-Verlag 1982, vol. 78, pp. 104-111.
Granik V.G., "Metabolism of Exogenous Compounds", Moscow, Vuzovskaya Kniga, 2006.
George A. Heise, "Behavioral Methods for Measuring Effects of Drugs on Learning and Memory in Animals", Medicinal Research Reviews ©1984 by John Wiley & Sons, Inc., vol. 4, No. 4, pp. 535-556.
Robert S. Hsu at al., "Identification of the Urinary Metabolites of Tacrine in the Rat", Drug Metabolism and Disposition © 1990 by The American Society for Pharmacology and Experimental Therapeutics, vol. 18, No. 5, pp. 779-783.
Krichevskii E.S. et al., Search for new drugs, "Synthesis and biological characterization of new N-acyl-thiazoldine-4-carboxylic acid derivatives", Pharmaceutical Chemistry Journal, 2007, vol. 41, No. 10, pp. 519-522.
Toshitaka Nabeshima, "Ameliorating Effects of Nefiracetam (DM-9384) on Brain Dysfunction", Drugs of Today vol. 30, No. 5, 1994, pp. 357-379.
Michael A. Rogawski et al., "The Neuropharmacological Basis for the Use of Memantine in the Treatment of Alzheimer's Disease", CNS Drug Reviews © 2003 Neva Press, Branford, Connecticut, vol. 9, No. 3, pp. 275-308.
S. Yu. Ryabova et al., "A new method for the synthesis of [1,4] diazepino [6,5-b] indole derivatives, Russian Chemical Bulletin", International Edition © 2006 Springer Science+Business Media, Inc., vol. 55, No. 12, Dec. 2006, pp. 2278-2284.
Tomoaki Sato et al., "Ameliorative and Exacerbating Effects of [pGlu4,Cyt6]AVP(4-9) on Impairment of Step-Through Passive Avoidance Task Performance by Group II Metabotropic Glutamate Receptor-Related Drugs in Mice", Journal of Pharacological Sciences © The Japanese Pharmacological Society, vol. 97, Jan. 5, 2005, pp. 437-442.
Kemal Sweidan et al., "Novel Derivatives of 1,3-Dimethyl-5-methylenebarbituric Acid", Letters in Organic Chemistry © Bentham Science Publishers Ltd., vol. 6, Nov. 5, 2009, pp. 669-672.
T.I. Vozyakova et al., "Synthesis and Pharmacological Properties of 2,3,4-Triaminopridine Derivatives", Pharmaceutical Chemistry Journal © 2006 Springer Science+Business Media, Inc., vol. 40, No. 12, 2006 pp. 645-649.
Cin D. World Science, 2007, No. 11, pp. 18-25.
PCT International Search Report for PCT/RU2011/000276; Mailed on Dec. 8, 2011; pp. 1-2.
PCT International Preliminary Report on Patentability and Written Opinion for PCT/RU2011/000276: Issued Nov. 6, 2012; pp. 1-7.

* cited by examiner

*Primary Examiner* — Kristin Bianchi
(74) *Attorney, Agent, or Firm* — Dergosits & Noah LLP

(57) ABSTRACT

The present invention relates to the field of chemical-pharmaceutical industry and medicine. An agent, exhibiting the properties of a cognitive function promoter, was selected from 1,3-dimethyl-5-[(4-pyridylamino)methylene]barbituric acid and 4-amino-1-(3-nitro-2-oxo-1-pheny-1,2-dihydro-1,6-naphthyridin-5-yl)pyridinium chloride. The compounds, that are proposed as agents, exhibit potent biological activity.

2 Claims, No Drawings

AGENT EXHIBITING THE PROPERTIES OF A COGNITIVE FUNCTION PROMOTER (EMBODIMENTS)

CROSS REFERENCE TO RELATED APPLICATION

This application is a U.S. National Phase of International Application No. PCT/RU2011/000276 filed on Apr. 28, 2011, which claims priority to and the benefit of Russian Patent Application No. 2010117541 filed on Apr. 30, 2010, the entire contents of which are incorporated herein by reference.

FIELD OF THE INVENTION

The present invention relates to the field of chemical-pharmaceutical industry and medicine and concerns compounds which can be used as a drug able to positively regulate the activity of Central Nervous System (CNS).

PRIOR ART

At the present time one of the most fundamental problems of contemporary biology is the study of laws of memory development in the brain. In this respect a very important task is to answer theoretical and practical question on how exactly does the activation of nerve cells ensures memory development [1]. Because of this, a main approach to solving this problem is synthesis and biological study of new original compounds, able to activate cognitive functions, and identification of general laws of synthesis of such substances and the possibility of their medical use.

A considerable number of substances, which can be used to control many functions of central nervous system (CNS) are known. Among them are different chemical compounds affecting psychical condition and emotions, reducing the sensitivity of painful sensations, improving sleep, causing narcosis, having anticonvulsive action, etc.

It is known that during different organic and functional disorders of central nervous system (weakness, reduction in intellectual functions), which currently can't be effectively treated by therapeutic means, drugs that activate cognitive functions can be used. In recent years it was found that during Alzheimer disease and other disorders, including different types of geriatric dementia, anti-cholinesterase drugs like tacrine, amiridine, donepezil may be used. These drugs are used during different dementias, but, as of now, mainly as adjunctive drugs.

Alzheimer disease includes the reduction of receptor activity of muscarinic M2 and nicotine receptors. The damage of cholinergic system is related to the reduced activity of choline acetyltransferase during this disease and high level of acetylcholine reuptake—all this leads to the decay of cognitive functions. At the present time the involvement of acetylcholine in learning and knowledge functions is shown in models.

Another approach should also be considered—the action on one of the subtypes of glutamate receptors—NMDA-receptors, hyper activation of which may lead to the activation of neurodegenerative symptoms [2, 3]. A considerable number of compounds were synthesized, which block the hyper activation of these receptors.

In particular, pyridine derivatives and medical products based on them, which exhibit selective blocking activity towards a subtype of NMDA-receptors (patent RU2303037, published 20 Jul. 2007), are described in the prior art. However these compounds can cause different adverse effects.

The compounds, most similar in the achieved results, are 4-amino- and 2,4-diaminopyridone derivatives that stimulate cognitive functions. These derivatives combine the properties of NMDA-receptor antagonists with the properties of moderate acetylcholinesterase inhibitors and the properties of agonists of nicotine receptors and sympathomimetics (EA200801639 (A1), published 2009 Aug. 28).

This reference can be designated as the closest analog.

SUMMARY OF THE INVENTION

The goal of this invention is to find new effective agents, the use of which may provide the means to treat such diseases, and also to find new compounds, that can positively affect memory functions, i.e. to find compounds that are cognitive function promoter.

The goal is achieved by the synthesis and biological research of new compounds which exhibit potent biological activity in vivo towards cognitive functions. These compounds are promising as agents, based on which new original medications can be created, which can positively regulate the activity of Central Nervous System (CNS).

DETAILED DESCRIPTION OF THE PRESENT INVENTION

Among many compounds, synthesized by us, a selection was performed based on the principle of most potent activity and high therapeutic index (the ratio of effective dose to toxic dose) and two most attractive compounds (1, 2) were chosen, which can be used as agents exhibiting the properties of activators of cognitive functions.

Thus, the objects of the invention are:
an agent, exhibiting the properties of activator of cognitive functions, that is a 1,3-dimethyl-5-[(4-pyridylamino)methylene]barbituric acid (1):

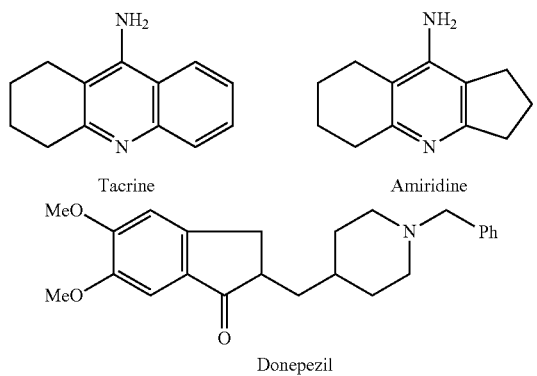

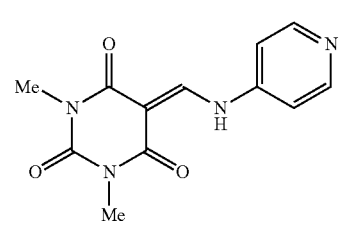

1 an agent, exhibiting the properties of activator of cognitive functions, that is a 4-amino-1-(3-nitro-2-oxo-1-pheny-1,2-dihydro-1,6-naphthyridin-5-yl)pyridinium chloride of formula (2):

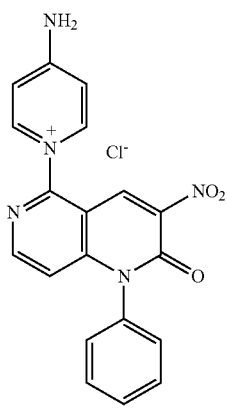

Methods of preparation the target compounds provide for the participation of 4-aminopyridine as an intermediate compounds for the creation of compounds having in their structures 4-aminopyridine fragments or 4-aminopyridinium fragments (compounds 1 and 2) and, accordingly, ensuring technologically acceptable conditions of synthesizing the target compounds from available raw materials and without implementing special conditions of the process.

The invention can be illustrated by the examples of embodiments shown below:

EXAMPLE 1

Preparation of 1,3-dimethyl-5-[(4-pyridylamino)methylene]barbituric acid (1)

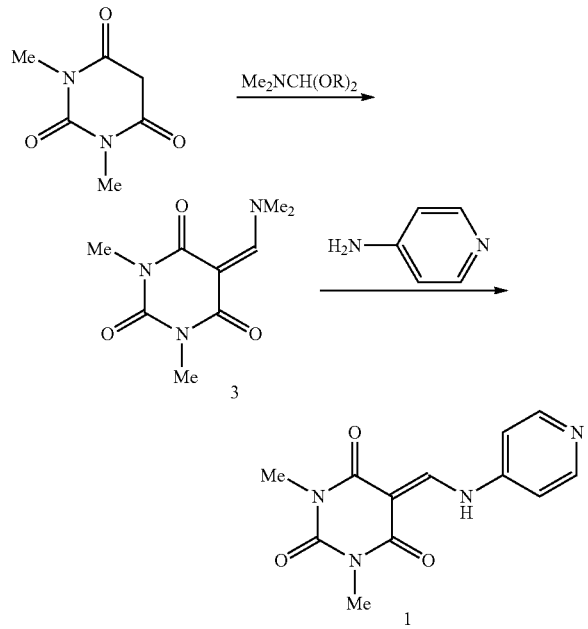

14.7 ml of dimethylformamide diethyl acetal (dimethylformamide dimethyl acetal also may be used) are added one drop at a time into a suspension of 7.8 g of 1,3-dimethylbarbituric acid in 50 ml of diethyl ether, the mixture is then stirred for 2 hours at room temperature and 9.82 g of enamine 3 are filtered. The mixture of 1.05 g of Compound 3 and 0.47 g of 4-aminopyridine are heated using oil bath to the bath temperature ≈160° C. and then held for 30 minutes at 160-170° C., 1.1 g (85%), m. p. 233-235° C. (from DMF).

$^1$H NMR (DMSO-$d_6$) δ, ppm: 3.21 (s, 6H, 2 CH$_3$), 8.09 (d, J=6.3 Hz, 2H, 2'-H), 8.74 (d, J=6.3 Hz, 2H, 3'-H), 8.77 (d, J=8.9 Hz, 1H, methylene), 12.13 (d, J=8.9 Hz, 1H, NH).

EXAMPLE 2

Preparation of 4-amino-1-(3-nitro-2-oxo-1-pheny-1,2-dihydro-1,6-naphthyridin-5-yl)pyridinium chloride (2)

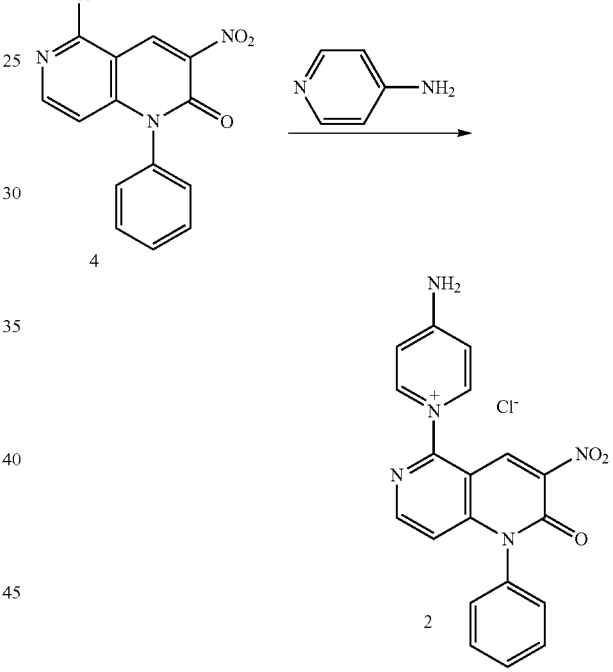

Method 1. A mixture of 0.26 g (0.86 mmol) of 5-chloro-3-nitro-1-phenyl-1,6-naphthyridin-2(1H)-one (4) and 0.16 g (1.70 mmol) of 4-aminopyridine in 20 ml of 2-propanol was refluxed for 4 hours. The precipitate does not dissolve during boiling. After cooling the reaction mixture to 20° C. the precipitate was filtered, washed with 2-propanol, DMF. 0.19 g (56%) of Compound 2 was obtained. M.p. 326-329° C.

ESI-MS, m/z: 360 [M+H]$^+$; 719 [2M+H]$^+$; 285 [M$^+$-NO$_2$—CO]. $^1$H NMR (DMSO-$d_6$) δ, ppm: 6.70 (d, J=6.13 Hz, 1H, 8'-H), 7.02 (d, J=7.20 Hz, 2H, 3-H+5-H), 7.38, 7.63 (both m, 2H and 3H, Ph), 8.38 (d, J=7.20 Hz, 2H, 2-H+6-H); 8.47 (d, J$_o$=6.13 Hz, 1H, 7'-H), 8.71 (s, 1H, 4'-H); 8.92 (br.s, 2H, NH$_2$). Found (%): C, 57.57; H, 3.99; N, 17.70. C$_{19}$H$_{14}$ClN$_5$O$_5$. Calc. (%): C, 57.66; H, 3.57; N, 17.69.

Method 2. A mixture of 0.15 g (0.50 mmol) of 5-chloro-3-nitro-1-phenyl-1,6-naphthyridin-2(1H)-one (4) and 0.05 g (0.50 mmol) of 4-aminopyridine in 15 ml of acetonitrile was refluxed for 86 hours. Control by TLC. The precipitate does not dissolve during boiling. After cooling the reaction mixture to 20° C. the precipitate was filtered, washed with acetonitrile. 0.14 g (72%) of analytically pure sample 2 was obtained. M. p. does not exhibit depression with the sample, obtained using method 1.

EXAMPLE 3

Study of the Activity of the Synthesized Compounds In Vivo

In order to study the activity of the synthesized compounds in vivo one of the most used methodologies of examination and assessment of activation of cognitive functions was used—improvement or easier development of conditioned passive avoidance response (CPAR) in animals. From the time of study of cognitive properties of nootropil and up to the present time, conditioned passive avoidance response (CPAR) is used more often than other behavioral procedures for studying and screening of drugs affecting the processes of learning and memory in rodents. CPAR is used for studying the action of drugs on learning (if the tested drug is administered before a training session), on saving or retention in memory (if the drug is administered after the training) and on memory retrieval (administering drugs before memory testing). This method is also used to study and test substances in models of disorders of learning and memory, caused by experimental brain dysfunction (GABA, cholinergic, induced by cholinergic toxin AF64A), alcohol-benzodiazepine induced, electrocution induced, hypoxia induced and age-related amnesias, inhibition of protein synthesis, etc. [4-6].

Thus, like other modern behavioral methods (operant, labyrinth, etc.), research using CPAR method aims to study and screen potential drugs, which can be used in cognitive disorders related to neurodegenerative diseases in animals (Alzheimer disease, multi-infarct dementia, Parkinson disease, Huntington's chorea, epilepsy, multiple sclerosis, etc.).

Because the cholinergic neurotransmitter system of the brain is involved in the neurochemical mechanisms of memory and learning, at the first stage it is important to study the activity of the selected compounds on nicotine-type acetylcholine receptors.

Among studies, dedicated to the use of CPAR methodology in order to study the activation of cognitive functions we would also note studies [7-13].

Performed studies have shown that the declared agents exhibit mnemotropic properties, allowing their use in the creation of drugs for treating disorders of cognitive functions.

Comparative study of the effects of compounds 1 and 2 on learning and memory of mice in tests of conditioned passive avoidance response (CPAR) in model of amnesia, induced by the administration of scopolamine—a blocker of central cholinergic receptors.

Studies were performed using 470 male mice, body mass 20-22 g, using 20 animals for one dose. CPAR conditioning of mice was performed using step down method [1], in a cell with electrode floor and avoidance area. Parameters of electric stimulation for animals leaving the safety area were 50 V during 3-5 sec. The criterion of learning and memory was the staying of the animal in the area during 1 minute when testing 2 hours after training and 24 hours after training.

Learning deficit was induced by the administration of scopolamine (1.0 mg/kg, intraperitoneal) 15 minutes before the training and by reduction in the number of animal training sessions to 2 instead of 5 (undertraining).

The duration of the mnemotropic action of the compounds in conditions of learning deficit was assessed by the number of animals in a group (in percents), staying in safety zone (with immobilization).

To assess their action of different phases of memory development (fixation, consolidation and reproduction) the tested compounds were administered before the training (before scopolamine) and immediately after the training. The tested compounds were administered intraperitoneally using 2 schedules: first—the compounds in doses 0.01-0.1 and 1.0 (or 3.0) mg/kg 40 minutes before the training and, correspondingly, 5 minutes before scopolamine, second—compounds in the same doses right after the training. Control was parallel in each series of experiments: one control group received saline solution instead of the tested compounds and scopolamine, second control group—scopolamine, using the same schedule and doses.

The dose of a tested compound was deemed effective when the number of positive reactions differed significantly from the reactions of the animals who received saline solution and scopolamine. Statistical analysis was conducted with significance of difference from negative control at $p<0.05$.

Results of the studies have shown that learning ability of control animals after $2^{nd}$ training session is about 80% and does not significantly change when testing after 2 hours and after 24 hours. The administration of a central choline blocker scopolamine caused the reduction of this indicator to an average of 28%, that is an evidence of the combined action of the drug (amnesia) and undertraining.

The tested compounds 1 and 2 have improved learning and memory of experimental animals during scopolamine-induced amnesia. There were no significant differences in effectiveness when testing learning and memory after 2 hours and after 24 hours. The compounds exhibited maximum effect in animals in low doses (0.01 mg/kg) and somewhat less marked effect in doses of 0.1 mg/kg and 1 mg/kg. Administration of the compounds before training and immediately after the training did not significantly change the intensity of mnemotropic effect in animals.

TABLE 1

Cognitive activity and acute toxicity of compounds of formulas 1 and 2

| Tested compounds | Doses, mg/kg, i/p | Number of animals with CPAR (%) | Acute toxicity i/p, mg/kg | Therapeutic index $LD_{50}$/Min. ED |
|---|---|---|---|---|
| Compound 1 | 0.01 | 90.0 | 15.3 ± 2.6 | 1530 |
|  | 0.1 | 80.0 | (11.7-21.0) |  |
|  | 1.0 | 60.0 | P < 0.05 |  |
|  | 10.0 | 50.0 |  |  |
| Compound 2 | 0.01 | 60 | 107.7 ± 14.1 | 10770 |
|  | 0.1 | 80 | (84.5-137.3) |  |
|  | 1.0 | 70 | P < 0.05 |  |
|  | 10.0 | 60 |  |  |
| Scopolamine | 1.0 | 35 | — | — |

Thus, the performed studies have shown the ability of the compounds to exhibit potent stimulating action on processes of learning and memory in animals. It was shown that all compounds exhibit stimulating action on the process of memory fixation as well as on consolidation or retention of information.

In addition, it is possible to create new original medications, which can positively affect memory improvement and learning ability, based on these compounds.

REFERENCES

1. Cin D. World of Science, 2007, No. 11, p. 18-25
2. Bachurin S. O., "Issues of medical chemistry", 2001, No. 2, p. 1-41
3. Granik V. G., Metabolism of exogenous compounds, Moscow, Vuzovskaya Kniga, 2006.
4. Nabeshima T.—Ameliorating Effects of Nefiracetam (DM-9384) on Brain Dys-function//Drugs of Today, 1994, 30(5), 357-379.
5. Heise G. A.—Behavioral Methods for Measuring Effects of Drugs on Learning and Memory in Animals//Medicinal Research Review, 1984, 4, 535-558.
6. Sato T, Ishida T, Tanaka K et al—Ameliorative and Exacerbating Effects of [pGlu4,Cyt6] AVP(4-9) on Impairment of Step-Through Passive Avoidance Task Performance by Group II Metabotropic Glutamate Receptor-Related Drugs in Mice//J. Pharmacol Sci, 2005, 97, 437-442.
7. Ryabova S. Y., Alexeeva L. M., Rastorgueva N. A., Lisicah E. A, Papakhin D. M., Parshin V. A., Granik V. G. A new method of synthesis of derivatives of [1,4]diazepino[6,5-b]indole, Bulletin of Academy of Sciences, Chemistry series, 2006, No. 12, p. 2193-2199
8. Vozyakova T. I., Alexeeva L. M., Parshin V. A., Kalinkina M. A., Granik V. G. Synthesis and pharmacological study of derivatives of 2,3,4-triaminopyridines, Chem. Pharm. Journal, 2006, No. 12, p. 8-12.
9. Andreeva N. I., Golovina S. M., Parshin V. A., Mashkovsky M. D. New data on psychopharmacological properties of the antidepressant azafen, Chem. Pharm. Journal, 1997, No. 3, p. 10-13.
10. Camps P., Munoz-Torrero D. Mini Reviews in Medicinal Chemistry, 2002, v. 2, p. 11.
11. Hsu R. S., Shutske G. M., Dileo E. M., Chesson S. M., Linville A. R., Allen R. C. Drug. Metab. Disposit, 1990, v. 18, No. 5, p. 779.
12. Rohawski M. A., Wenk C. L. CNS Drug Reviews, 2003, v. 9, No. 3, p. 275-308.
13. Cumin R., Bandle E. F., Gamzu E. and Haefely W. E.// Psychopharmacology (Berl.), 1982.-v. 78-p. 104-111.

The invention claimed is:

1. An agent, exhibiting the properties of a cognitive function promoter, that is a 1,3-dimethyl-5-[(4-pyridylamino)methylene]barbituric acid of formula (1)

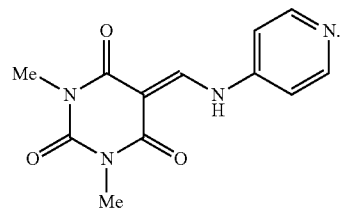

2. An agent, exhibiting the properties of a cognitive function promoter, that is a 4-amino-1-(3-nitro-2-oxo-1-pheny-1,2-dihydro-1,6-naphthyridin-5-yl)pyridinium chloride of formula (2)

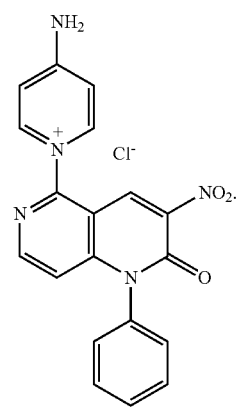

* * * * *